US008888687B2

(12) United States Patent
Ostrovsky et al.

(10) Patent No.: US 8,888,687 B2
(45) Date of Patent: Nov. 18, 2014

(54) METHOD AND APPARATUS RELATED TO A FLEXIBLE ASSEMBLY AT A DISTAL END PORTION OF A MEDICAL DEVICE

(75) Inventors: Isaac Ostrovsky, Wellesley, MA (US); Ty Fairneny, Hopkinton, MA (US); Victor Shukhat, Canton, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 700 days.

(21) Appl. No.: 12/913,182

(22) Filed: Oct. 27, 2010

(65) Prior Publication Data
US 2011/0098529 A1    Apr. 28, 2011

Related U.S. Application Data

(60) Provisional application No. 61/255,655, filed on Oct. 28, 2009.

(51) Int. Cl.
*A61B 1/00* (2006.01)
*A61B 1/018* (2006.01)
*A61B 1/005* (2006.01)
*A61B 1/04* (2006.01)
*A61B 1/07* (2006.01)

(52) U.S. Cl.
CPC .............. *A61B 1/018* (2013.01); *A61B 1/0008* (2013.01); *A61B 1/0055* (2013.01); *A61B 1/07* (2013.01)
USPC ............................ 600/129; 600/106; 600/127

(58) Field of Classification Search
CPC . A61B 1/00149; A61B 1/00154; A61B 1/018
USPC ......... 600/106, 129, 104, 107, 114, 127, 137, 600/139, 141, 142, 149
See application file for complete search history.

(56) References Cited

U.S. PATENT DOCUMENTS

| | | | |
|---|---|---|---|
| 5,005,558 A | 4/1991 | Aomori | |
| 5,271,382 A | 12/1993 | Chikama | |
| 5,403,342 A | 4/1995 | Tovey et al. | |
| 5,477,856 A | 12/1995 | Lundquist | |
| 5,674,182 A * | 10/1997 | Suzuki et al. | 600/129 |
| 5,857,964 A | 1/1999 | Konstorum et al. | |
| 5,860,995 A | 1/1999 | Berkelaar | |
| 5,873,817 A | 2/1999 | Kokish et al. | |
| 5,938,588 A | 8/1999 | Grabover et al. | |
| 6,171,235 B1 | 1/2001 | Konstorum et al. | |
| 6,447,444 B1 * | 9/2002 | Avni et al. | 600/121 |
| 6,475,140 B1 | 11/2002 | Konstorum et al. | |
| 6,485,411 B1 | 11/2002 | Konstorum et al. | |
| 6,497,651 B1 * | 12/2002 | Kan et al. | 600/114 |
| 6,656,195 B2 | 12/2003 | Peters et al. | |
| 6,740,030 B2 | 5/2004 | Martone et al. | |

(Continued)

*Primary Examiner* — Alireza Nia
(74) *Attorney, Agent, or Firm* — Bookoff McAndrews, PLLC

(57) ABSTRACT

In one embodiment, an apparatus may include an endoscopic housing defining an opening disposed along a plane substantially normal to a longitudinal axis of the endoscopic housing. A rotatable member may be coupled to the endoscopic housing and may have a proximal portion configured to move from a stowed configuration to a deployed configuration when the proximal portion of the rotatable member is rotated about an axis substantially normal to the longitudinal axis of the endoscopic housing. The proximal portion of the rotatable member may be disposed on a distal side of the plane when in the stowed configuration and disposed on a proximal side of the plane associated with the opening when in the deployed configuration.

13 Claims, 8 Drawing Sheets

(56) References Cited

U.S. PATENT DOCUMENTS

| | | |
|---|---|---|
| 6,749,560 B1 | 6/2004 | Konstorum et al. |
| 6,780,151 B2 | 8/2004 | Grabover et al. |
| 6,790,173 B2 | 9/2004 | Saadat et al. |
| 6,817,974 B2 | 11/2004 | Cooper et al. |
| 6,858,005 B2 | 2/2005 | Ohline et al. |
| 6,890,329 B2 | 5/2005 | Carroll et al. |
| 7,090,637 B2 | 8/2006 | Danitz et al. |
| 8,092,371 B2 * | 1/2012 | Miyamoto et al. ............ 600/106 |
| 8,591,399 B2 * | 11/2013 | Marescaux et al. ........... 600/106 |
| 2004/0138529 A1 * | 7/2004 | Wiltshire et al. ............. 600/144 |
| 2004/0186350 A1 | 9/2004 | Brenneman et al. |
| 2004/0199052 A1 | 10/2004 | Banik et al. |
| 2004/0225186 A1 | 11/2004 | Horne, Jr. et al. |
| 2004/0236316 A1 | 11/2004 | Danitz et al. |
| 2005/0015072 A1 | 1/2005 | Engel et al. |
| 2005/0090809 A1 | 4/2005 | Cooper et al. |
| 2005/0096502 A1 * | 5/2005 | Khalili ......................... 600/106 |
| 2005/0096694 A1 | 5/2005 | Lee |
| 2005/0107667 A1 | 5/2005 | Danitz et al. |
| 2005/0119644 A1 | 6/2005 | Koerner |
| 2005/0131279 A1 | 6/2005 | Boulais et al. |
| 2005/0182475 A1 | 8/2005 | Jen et al. |
| 2005/0187575 A1 | 8/2005 | Hallbeck et al. |
| 2005/0272977 A1 * | 12/2005 | Saadat et al. .................. 600/114 |
| 2005/0273084 A1 | 12/2005 | Hinman et al. |
| 2005/0273085 A1 | 12/2005 | Hinman et al. |
| 2006/0041188 A1 | 2/2006 | Dirusso et al. |
| 2006/0094931 A1 | 5/2006 | Danitz et al. |
| 2006/0111209 A1 | 5/2006 | Hinman et al. |
| 2006/0111210 A1 | 5/2006 | Hinman |
| 2006/0111615 A1 | 5/2006 | Danitz et al. |
| 2006/0111616 A1 | 5/2006 | Danitz |
| 2008/0269562 A1 * | 10/2008 | Marescaux et al. ........... 600/142 |
| 2008/0287741 A1 | 11/2008 | Ostrovsky et al. |
| 2009/0292164 A1 * | 11/2009 | Yamatani ...................... 600/106 |
| 2010/0081874 A1 * | 4/2010 | Miyamoto et al. ............ 600/109 |

* cited by examiner

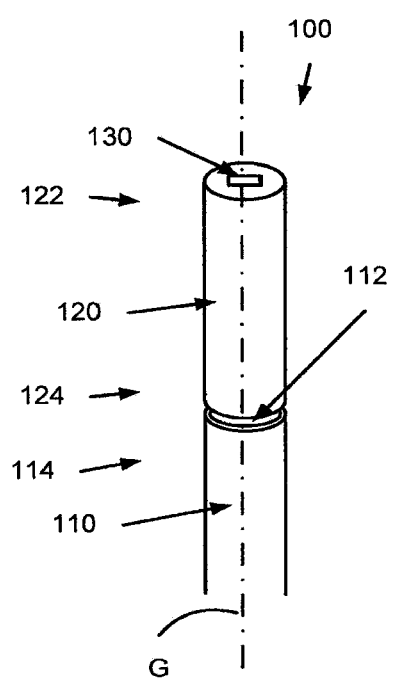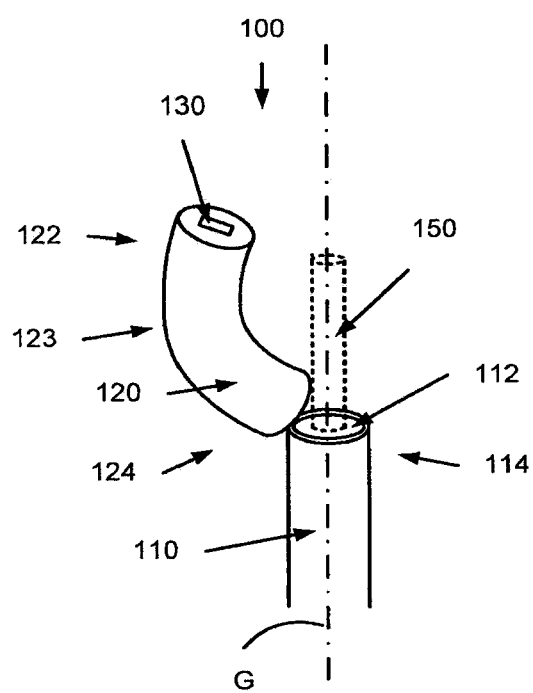
FIG. 1A
FIG. 1B

METHOD AND APPARATUS RELATED TO A FLEXIBLE ASSEMBLY AT A DISTAL END PORTION OF A MEDICAL DEVICE

CROSS REFERENCE TO RELATED APPLICATION

This patent application claims the benefit of priority under 35 U.S.C. §119 to U.S. Provisional Patent Application No. 61/255,655, entitled METHOD AND APPARATUS RELATED TO A FLEXIBLE ASSEMBLY AT A DISTAL END PORTION OF A MEDICAL DEVICE, filed Oct. 28, 2009, the entirety of which is incorporated herein by reference.

FIELD OF THE INVENTION

Embodiments relate generally to medical devices, and, in particular, to a medical device that has a flexible portion that can be used within a body of a patient.

BACKGROUND OF THE INVENTION

A medical practitioner may be required to make multiple incisions in a body of a patient through which the medical practitioner can access an area within the body to be treated during a medical procedure. For example, a medical practitioner may be required to make multiple separate incisions through which multiple known tools, such as an imaging tool, a light tool, a cutting tool, an extraction tool, and/or so forth, can be inserted into and/or removed from a body of a patient at various times (e.g., during overlapping time periods, during mutually exclusive time periods) during a laparoscopy procedure. Making and using multiple separate incisions, however, can not only increase the recovery time of the patient after a medical procedure, but can also increase a duration of the medical procedure and/or a risk of complications during the medical procedure.

Thus, a need exists for methods and apparatus that can enable a medical practitioner to, for example, reduce the number of incisions required during a medical procedure.

SUMMARY OF THE INVENTION

An aspect of the present disclosure includes an apparatus which may include an endoscopic housing defining an opening disposed along a plane substantially normal to a longitudinal axis of the endoscopic housing. The apparatus may further include a rotatable member coupled to the endoscopic housing which may have a proximal portion configured to move from a stowed configuration to a deployed configuration when the proximal portion of the rotatable member is rotated about an axis substantially normal to the longitudinal axis of the endoscopic housing. Further, the proximal portion of the rotatable member may be disposed on a distal side of the plane when in the stowed configuration and may be disposed on a proximal side of the plane associated with the opening when in the deployed configuration.

Various embodiments of the disclosure may include one or more of the following aspects: the proximal portion of the rotatable member may have a proximal surface configured to be in contact with an outer surface of a wall of the endoscopic housing when the rotatable member is in the deployed configuration; the rotatable member may be configured to move from the stowed configuration to the deployed configuration when the rotatable member is rotated in a first direction, and the rotatable member may be configured to move from the deployed configuration to the stowed configuration when the rotatable member is rotated in a second direction opposite the first direction; the proximal portion of the rotatable member may include a substantially flat proximal surface that is non-parallel to the longitudinal axis of the endoscopic housing when the rotatable member is in the stowed configuration, and the substantially flat proximal surface of the proximal portion of the rotatable member may be substantially parallel to the longitudinal axis of the endoscopic housing when the rotatable member is in the deployed configuration; the apparatus may further include a pull wire coupled to the rotatable member and configured to move the rotatable member from the stowed configuration to the deployed configuration; the apparatus may further include an articulation assembly coupled to the endoscopic housing and defined by a plurality of links collectively coupled in series, and the rotatable member may be a proximal end link of the plurality of links; the rotatable member may be included in an articulation assembly coupled to the endoscopic housing, and the apparatus may further include one of an electromagnetic radiation source and an electromagnetic radiation sensor coupled to a distal end portion of the articulation assembly; the rotatable member may be a first rotatable member, where the first rotatable member may be configured to rotate in a first direction about the longitudinal axis, and the apparatus may further include a second rotatable member having a proximal portion which may be configured to move from the distal side of the plane to the proximal side of the plane when rotated in a second direction opposite the first direction; and the opening may be in fluid communication with a working channel defined by the endoscopic housing.

Another aspect of the present disclosure includes an apparatus which may have an endoscopic housing defining a lumen in fluid communication with a distal opening of the endoscopic housing. The apparatus may further include an articulation assembly which may be coupled to the endoscopic housing and which may have a portion substantially disposed within a space distal to the distal opening of the endoscopic housing when the articulation assembly is in a stowed configuration. The portion of the articulation assembly may further be configured to be disposed outside of the space when the articulation assembly is in a deployed configuration such that a portion of a tool moved from within the lumen of the endoscopic housing is disposed within the space.

Various embodiments of the disclosure may include one or more of the following aspects: the portion of the articulation assembly may be substantially disposed within the space such that the space includes a portion of a longitudinal axis of the endoscopic housing; the portion of the articulation assembly may be a proximal end portion of the articulation assembly; the apparatus may further include a cover disposed around a section of the articulation assembly when the articulation assembly is in the stowed configuration; the portion of the articulation assembly may be substantially disposed within the space such that the space includes a portion of a longitudinal axis of the endoscopic housing, and the portion of the articulation assembly may be a proximal end portion of the articulation assembly and the articulation assembly may further include a distal end portion disposed away from the longitudinal axis when the articulation assembly is in the deployed configuration; the articulation assembly may have two inflection points when in the deployed configuration; and the articulation assembly may be a first articulation assembly, the apparatus may further include a second articulation assembly coupled to the endoscopic housing and having a portion substantially disposed within the space when the second articulation assembly is in a stowed configuration, and the second articulation assembly may be configured to move outside of the space when the second articulation assembly is changed from the stowed configuration to a deployed configuration.

A further aspect of the present disclosure includes an apparatus which may have an endoscopic housing defining a lumen in fluid communication with a distal opening of the endoscopic housing. The apparatus may further include an articulation assembly coupled to the endoscopic housing and having a proximal end portion disposed distal to the distal opening of the endoscopic housing. Additionally, the apparatus may include a cover having a portion disposed around a portion of the articulation assembly when the cover is in a first position, the portion of the cover being disposed around a portion of the endoscopic housing when the cover is in a second position.

Various embodiments of the disclosure may include one or more of the following aspects: the cover may be configured to be slidably moved along a longitudinal axis of the endoscopic housing from the first position to the second position; the articulation assembly may be substantially straight when the cover is in the first position, and the articulation assembly may have at least one inflection point when the cover is in the second position and the articulation assembly is in the deployed configuration; the articulation assembly may be substantially prevented from changing from a stowed configuration to a deployed configuration when the portion of the cover is in the first position; and the cover may be configured to be lockably coupled to a locking mechanism when in the second position.

Another aspect of the present disclosure includes an apparatus which may have an endoscopic housing defining a working channel in fluid communication with a distal opening of the endoscopic housing. The apparatus may further include a first articulation assembly coupled to the endoscopic housing which may have a portion disposed distal to the distal opening, a first electromagnetic radiation sensor coupled to the first articulation assembly, a second articulation assembly coupled to the endoscopic housing which may have a portion disposed distal to the distal opening, and a second electromagnetic radiation sensor coupled to the second articulation assembly.

Various embodiments of the disclosure may include one or more of the following aspects: the first electromagnetic radiation sensor may be configured to produce a first signal of a stereoscopic image in response to electromagnetic radiation, and the second electromagnetic radiation sensor may be configured to produce a second signal of the stereoscopic image in response to the electromagnetic radiation; the apparatus may further include an electromagnetic radiation source coupled to the first articulation assembly, where the first electromagnetic radiation sensor and the second electromagnetic radiation sensor may each be configured to produce a signal in response to electromagnetic radiation reflected from an object after being emitted from the electromagnetic radiation source; the first electromagnetic radiation sensor may be coupled to a distal end portion of the first articulation assembly; the first articulation assembly and the second articulation assembly may collectively define a stowed configuration and may collectively define a deployed configuration, and the first electromagnetic radiation sensor may have a field of view that intersects a field of view of the second electromagnetic radiation sensor when the first articulation assembly and the second articulation assembly are in the deployed configuration; the first articulation assembly and the second articulation assembly may collectively define a stowed configuration and may collectively define a deployed configuration and the apparatus may further include an actuator coupled to the first articulation assembly and the second articulation assembly, where the first articulation assembly and the second articulation assembly may be substantially simultaneously moved from the stowed configuration to the deployed configuration when the actuator is activated.

Another aspect of the present disclosure may include a method of moving a proximal end portion of an articulation assembly from a position disposed within a region distal to an opening of an endoscopic housing to a position substantially outside of the region, and the articulation assembly may be coupled to the endoscopic housing. The moving may further include moving in a lateral direction relative to a longitudinal axis of the endoscopic housing, the region being defined by a volume projected distally from the opening of the endoscopic housing along the longitudinal axis of the endoscopic housing. The method may also include moving a portion of a tool from within a lumen of the endoscopic housing into the region after the moving associated with the proximal end portion of the articulation assembly.

Various embodiments of the disclosure may include one or more of the following aspects: the method may further include inserting the articulation assembly into a body of a patient, where the moving associated with the proximal end portion of the articulation assembly may be performed after the inserting; the method may further include moving at least a portion of a cover from a position around the articulation assembly to a position around the endoscopic housing before the moving associated with the proximal end portion of the articulation assembly; and the method may further include receiving a signal from an electromagnetic radiation sensor at a distal end portion of the articulation assembly and producing a stereoscopic image based on the signal.

A further aspect of the present disclosure includes an apparatus which may have an endoscopic housing defining a working channel in fluid communication with a distal opening of the endoscopic housing. The apparatus may further include an articulation assembly coupled to the endoscopic housing and having a proximal portion disposed distal to the distal opening, the articulation assembly may also include a first link and a second link different than the first link, and the first link may have an asymmetrical wedge-shaped surface different than an asymmetrical wedge-shaped surface associated with the second link.

Various embodiments of the disclosure may include one or more of the following aspects: the asymmetrical wedge-shaped surface associated with the first link may be an asymmetrical wedge-shaped recess which may be configured to be coupled to a pivot point of the second link; the first link may be configured to rotate in a first direction about an axis substantially normal to a longitudinal axis of the endoscopic housing, and the second link may be configured to rotate in a second direction opposite the first direction; the apparatus may further include a first actuator coupled to the first link, the first link may be configured to rotate in a first direction about an axis substantially normal to a longitudinal axis of the endoscopic housing when the first actuator is activated, and a second actuator coupled to the second link, the second link may be configured to rotate in a second direction opposite the first direction when the second actuator is activated; and the apparatus may further include a first actuator coupled to the first link, the first link may be configured to rotate in a first direction about an axis substantially normal to a longitudinal axis of the endoscopic housing when the first actuator is activated, and a second actuator coupled to the second link, the second link may be configured to rotate in a second direction opposite the first direction when the second actuator is activated and the second actuator may be configured to be activated after the first actuator is activated.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

FIG. 1A is a schematic diagram that illustrates a flexible assembly coupled to an endoscopic housing when the flexible assembly is in a stowed configuration, according to an embodiment.

FIG. 1B is a schematic diagram that illustrates the flexible assembly coupled to the endoscopic housing shown in FIG. 1A when the flexible assembly is in a deployed configuration, according to an embodiment.

DESCRIPTION OF THE EMBODIMENTS

Figure 2A:
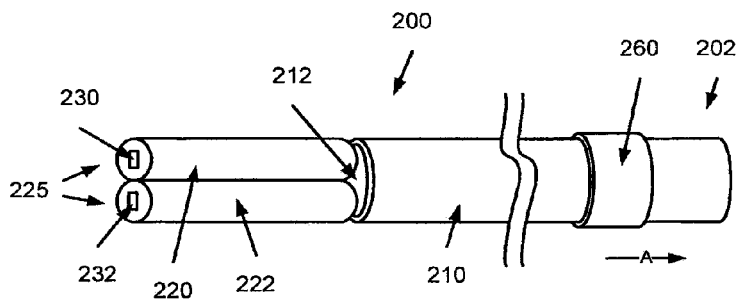
FIG. 2A is a schematic diagram that illustrates an endoscopic assembly that has two flexible assemblies in a stowed configuration, according to an embodiment.

Reference will now be made in detail to the present embodiments (exemplary embodiments) of the invention, examples of which are illustrated in the accompanying drawings. Wherever possible, the same reference numbers will be used throughout the drawings to refer to the same or like parts.

A distal end portion of a medical device, such as an endoscope, can have a flexible assembly configured to be inserted into a body of a patient and configured to move between one or more configurations. One or more components such as an electromagnetic radiation sensor and/or an electromagnetic radiation detector can be coupled to the flexible assembly of the medical device. In some embodiments, for example, the flexible assembly can be configured to move between a first configuration (e.g., a stowed configuration) and a second configuration (e.g., a deployed configuration). In some embodiments, the flexible assembly can be made of, for example, a monolithic flexible material or can be made of a series of links. If the flexible assembly includes a series of links, the flexible assembly can be referred to as an articulation assembly. In some embodiments, the distal end portion of the medical device can have more than one flexible assembly.

In some embodiments, a flexible assembly at a distal end portion of a medical device can be configured to move a component coupled to the flexible assembly (e.g., coupled to a distal end of the flexible assembly) to a specified position (e.g., a user-defined position) after the flexible assembly has been, for example, inserted into a body of a patient. For example, if an image sensor is coupled to a flexible assembly at a distal end portion of an endoscopic housing of an endoscope, the flexible assembly can be configured to move the image sensor to a specified orientation with respect to the endoscopic housing. In some embodiments, a flexible assembly can be configured so that one or more working channels of, for example, an endoscope, to which the flexible assembly is coupled, can be at least partially exposed (e.g., uncovered) when the flexible assembly is moved (e.g., moved in a predefined fashion).

In some embodiments, a medical device (such as an endoscope) with one or more flexible assemblies, one or more components, and/or one or more working channels can be used during one or more phases of a medical procedure via a single incision of a patient and/or after a single insertion into a body of a patient. For example, an endoscope can have a light source (e.g., a light emitting diode (LED), a light filament, a fiber optic light source) coupled to a first flexible assembly, an image sensor coupled to a second flexible assembly, and an opening of a working channel that can be exposed (e.g., uncovered) when the flexible assemblies are in a deployed configuration (and covered when the flexible assemblies are in a stowed configuration). The flexible assemblies of the endoscope can be inserted into an incision within a body of a patient by a medical practitioner while the flexible assemblies are in a stowed configuration. After being moved into desirable position within the body of the patient, the flexible assemblies can be moved from the stowed configuration (e.g., a predefined stowed configuration) to a deployed configuration (e.g., a predefined deployed configuration) to expose the opening of the working channel. A tool can be introduced into the body of the patient through the opening of the working channel by the medical practitioner so that the medical practitioner can perform a procedure related to or within an interior portion of the body of the patient. The light source coupled to the first flexible assembly (when in the deployed configuration) can be used to illuminate the interior portion and the image sensor coupled to the second flexible assembly (when in the deployed configuration) can be used by the medical practitioner to view the illuminated interior portion while the procedure is being performed.

It is noted that, as used in this written description and the appended claims, the singular forms "a," "an" and "the" include plural referents unless the context clearly dictates otherwise. Furthermore, the words "proximal" and "distal"

refer to a direction closer to and away from, respectively, an operator (e.g., a medical practitioner, a nurse, a technician, etc.) who can insert a medical device into a patient. Thus, for example, an end of an endoscope inserted inside a patient's body would be the distal end of the endoscope, while an end of the endoscope outside the patient's body would be the proximal end of the endoscope.

FIG. 1A and FIG. 1B are schematic diagrams that illustrate a flexible assembly 120 coupled to an endoscopic housing 110. Specifically, FIG. 1A is a schematic diagram that illustrates the flexible assembly 120 coupled to the endoscopic housing 110 when the flexible assembly 120 is in a stowed configuration, according to an embodiment. FIG. 1B is a schematic diagram that illustrates the flexible assembly 120 coupled to the endoscopic housing 110 when the flexible assembly 120 is in a deployed configuration, according to an embodiment. The flexible assembly 120 can be configured to change from the stowed configuration (shown in FIG. 1A) to the deployed configuration (shown in FIG. 1B), and vice versa, in response to being actuated via, for example, a pull-wire, a motor, a lever, and/or so forth.

The flexible assembly 120 and at least a portion of the endoscopic housing 110 can collectively be referred to as an endoscopic assembly 100. The endoscopic assembly 100 can be used during a minimally invasive surgery such as a laparoscopic surgery or a thoracoscopic surgery. In some embodiments, the endoscopic assembly 100 can be used during, for example, an exploratory portion of a medical procedure and/or during a surgery portion of a medical procedure. A distal end of the endoscopic assembly 100 is at the top end of FIGS. 1A and 1B.

As shown in FIG. 1A, when the flexible assembly 120 is in the stowed configuration, the flexible assembly 120 is disposed distal to (e.g., in front of, over) an opening 112 defined by the endoscopic housing 110. Specifically, a proximal end of the flexible assembly 120 is disposed distal to (e.g., substantially distal to) the opening 112 of the endoscopic housing 110. The opening 112 is at a distal end 114 of the endoscopic housing 110 and is in fluid communication with a lumen (not shown in FIG. 1A) defined by the endoscopic housing 110. Because the flexible assembly 120 is disposed distal to the opening 112 when in the stowed configuration, the opening 112 cannot be readily accessed (readily accessed from a region distal to the opening 112) when the flexible assembly 120 is in the stowed configuration. In other words, the opening 112 is substantially covered by (e.g., between 90%-100% covered by, 80% covered by, 60% covered by) the flexible assembly 120 so that it cannot be readily accessed when the flexible assembly is in the stowed configuration. Also, as shown in FIG. 1A, the flexible assembly 120 is aligned along (e.g., substantially aligned along) a longitudinal axis G (or centerline) of the distal end 114 of the endoscopic housing 110 when the flexible assembly 120 is in the stowed configuration.

In some embodiments, the lumen defined by the endoscopic housing 110 can function as a working channel. In some embodiments, the endoscopic housing 110 can define multiple working channels that can be exposed (exposed to a region distal to the endoscopic housing 110) when the flexible assembly 120 is moved from the stowed configuration to the deployed configuration. Accordingly, the endoscopic housing 110 can define multiple openings such as opening 112. In some embodiments, the endoscopic housing 110 can be made of a relatively rigid material and/or a relatively soft material. In some embodiments, the endoscopic housing 110 can be made of a metallic material and/or a polymer-based material such as a plastic.

As shown in FIG. 1B, at least a portion of the proximal end 124 of the flexible assembly 120 is moved from a position distal to the opening 112 of the endoscopic housing 110 when the flexible assembly 120 is moved from the stowed configured to the deployed configuration. As shown in FIG. 1B, the flexible assembly 120 is moved from a position substantially aligned along the longitudinal axis G (or centerline) of the proximal end 114 of the endoscopic housing 110 when the flexible assembly 120 is in the deployed configuration. Accordingly, a significant portion of the opening 112 of the endoscopic housing 110 is exposed (when viewed from a distal end of the endoscopic assembly 100) when the flexible assembly 120 is in the deployed configuration. The portion of the opening 112 that is exposed is more (e.g., significantly more) than a portion of the opening 112 that is exposed when the flexible assembly 120 is in the stowed configuration. For example, 50-100% of the opening 112 can be exposed when the flexible assembly 120 is in the stowed configuration.

When the flexible assembly 120 is moved from the stowed configuration to the deployed configuration, at least a portion of the flexible assembly 120 is configured to move in a lateral direction (or in a direction that has a lateral component) relative to the longitudinal axis G of the endoscopic housing 110. In other words, at least a portion of the flexible assembly 120 is configured to move in a lateral direction (or in a direction that has a lateral component) away from (e.g., translate away from) the longitudinal axis G of the endoscopic housing 110 when being moved from the stowed configuration to the deployed configuration. At least a portion of the flexible assembly 120 is configured to move in a lateral direction (or in a direction that has a lateral component) towards the longitudinal axis G of the endoscopic housing 110 when being moved from the deployed configuration to the stowed configuration. In some embodiments, at least a portion of the flexible assembly 120 is configured to rotate when being moved from the stowed configuration to the deployed configuration, and vice versa.

As shown in FIG. 1B, the flexible assembly 120 can have a single inflection point 123 when in the deployed configuration. In other words, the flexible assembly 120 can have substantially only one bend when in the deployed configuration. Although not shown, in some embodiments, the flexible assembly 120 can have multiple inflection points when in the deployed configuration. In some embodiments, the flexible assembly 120 can have one or more inflection points when in the stowed configuration.

As shown in FIG. 1B, the flexible assembly 120 is disposed outside of a region 150 (e.g., a volume) distal to the endoscopic housing 110 when in the deployed configuration. The region 150 can be defined by a volume projected distally from the opening 112 of the endoscopic housing 110 substantially along the longitudinal axis G of the endoscopic housing 110. When the flexible assembly 120 is disposed outside of (e.g., in a position substantially outside of) the region 150, an object, such as a tool, can be moved into the region 150 from within the endoscopic housing 110 via the opening 112 and/or from outside of the endoscopic housing 110. In contrast, the flexible assembly 120 is disposed within the region 150 when the flexible assembly 120 is in the stowed configuration (region 150 not shown in FIG. 1A). Accordingly, a tool can be passed from within the endoscopic housing 110 through the opening 112 into the region 150 (and at least portions of the tool can be moved outside of the region 150) when the flexible assembly 120 is in the deployed configuration, and the tool cannot be passed from within the endoscopic housing 110 through the opening 112 into the region 150 when the flexible assembly 120 is in the stowed configuration.

In some embodiments, the flexible assembly 120 can be in the stowed configuration when the endoscopic assembly 100 is moved into a body of a patient (not shown). The flexible assembly 120 can be substantially aligned with the longitudinal axis G (or centerline) of the endoscopic housing 110 (in the stowed configuration) so that endoscopic assembly 100 can be inserted into the body of the patient with relative ease. In some embodiments, the endoscopic assembly 100 can be directly inserted into the body of the patient or inserted into the body of the patient through, for example, a tubular member (e.g., a cannula) defining a working channel with an incision (different from a working channel defined by the endoscopic assembly 100). After the flexible assembly 120 is disposed within the body of the patient, the flexible assembly 120 can be moved from the stowed configuration to the deployed configuration so that, for example, a tool can be introduced into the body of the patient through the opening 112 of the endoscopic housing 110 (something that may not be performed when the flexible assembly 120 is in the stowed configuration).

Although not shown, in some embodiments, the flexible assembly 120 and/or the opening 112 can be included in a different portion of the endoscopic assembly 100. For example, a flexible assembly can be disposed in front of an opening in a medial portion of an endoscopic assembly. In some embodiments, the opening can still be an opening facing in a distal direction relative to the endoscopic assembly. For example the opening can be associated with a separate tube connected to and aligned along an axis parallel to the longitudinal axis (or centerline) G of the endoscopic assembly 100.

In some embodiments, the flexible assembly 120 can be made of a flexible material (e.g., a relatively soft and/or elastic material) such as a flexible polymer-based material. In some embodiments, the flexible assembly 120 can be monolithically formed of a material or can include links collectively coupled in series. If the flexible assembly 120 includes links, the links can be, for example, rotatable members, and can be referred to as a such. In some embodiments, the links can be made of a rigid material (e.g., a metallic material, a rigid polymer-based material) and/or a soft material (e.g., a soft polymer-based material).

In some embodiments, if the flexible assembly 120 is defined by a series of links, the links can be rotated and/or translated (with respect to one another and/or the endoscopic housing 110) in a first predefined fashion to define the stowed configuration of the flexible assembly 120, and can be rotated and/or translated in a second predefined fashion (different from the first predefined fashion) to define the deployed configuration of the flexible assembly 120. Accordingly, the flexible assembly 120 can be changed from the stowed configuration (e.g., a predefined stowed configuration) to the deployed configuration (e.g., a predefined deployed configuration), and vice versa, by rotating and/or translating the links. More details related to rotatable members (such as links) that can be used to define at least a portion of a flexible assembly are described below in connection with FIG. 6A through FIG. 10, and are described in co-pending U.S. patent application Ser. No. 12/121,345, filed May 15, 2008, entitled, "Articulating Torqueable Hollow Device," which is incorporated herein by reference in its entirety.

As shown in FIGS. 1A and 1B, the flexible assembly has a component 130 coupled to a distal end 122 of the flexible assembly 120. The component 130 can be any type of electronic component and/or mechanical component that can be used during, for example, a medical procedure. In some embodiments, the component 130 can be, for example, an electromagnetic radiation source (e.g., a light source, an ultra-violet ray source) configured to illuminate, for example, an interior portion of a body of a patient. In some embodiments, the component 130 can be, for example, an electromagnetic radiation sensor (e.g., an image sensor) configured to define a signal based on, for example, electromagnetic radiation reflected from an interior portion of a body of a patient. In some embodiments, the component 130 can be tool such as a cutting tool or an extraction tool.

Although not shown, in some embodiments, multiple components (such as component 130) can be coupled to the distal end 122 of the flexible assembly 120. Although not shown, in some embodiments, one or more components can be coupled to a different portion (e.g., a side portion) of the flexible assembly 120 (and/or the distal end 122 of the flexible assembly 120). For example, one or more components (such as component 130) can be coupled to medial portion and/or to a proximal portion of the flexible assembly. In some embodiments, a component can be coupled to a side wall of the flexible assembly 120 and/or can have at least a portion embedded within the flexible assembly 120.

In some embodiments, the flexible assembly 120 can be configured to move the component 130 into a specified position relative to, for example, the distal end 114 of the endoscopic housing 110 when the flexible assembly 120 is in the deployed configuration and/or the stowed configuration. For example, in instances where the component 130 is an image sensor, the flexible assembly 120 can be configured so that a focal length of the image sensor has a specified orientation with respect to the distal end 114 of the endoscopic housing 110 when the flexible assembly 120 is in the deployed configuration and/or the stowed configuration. Similarly, in instances where the component 130 is a light source, the flexible assembly 120 can be configured so that the light source can illuminate a specified region with respect to the distal end 114 of the endoscopic housing 110 when the flexible assembly 120 is in the deployed configuration and/or the stowed configuration. More details related to a flexible assembly configured to move a component to a specified position with respect to, for example, an endoscopic housing are described in connection with FIGS. 6A and 6B.

In some embodiments, endoscopic assembly 100 can be configured so that the component 130 is activated when the flexible assembly 120 is moved to deployed configuration and/or the stowed configuration. For example, in instances where the component 130 is a light source, the endoscopic assembly 100 can be configured so that the light source is activated in response to the flexible assembly 120 being changed from the stowed configuration to the deployed configuration, or vice versa. The endoscopic assembly 100 can be configured so that the light source is deactivated in response to the flexible assembly 120 being changed from the deployed configuration to the stowed configuration, or vice versa. Although not shown, in some embodiments, the component 130 can be activated using, for example, a switch at a proximal end of the endoscopic assembly 100 that is activated when the device is activated. More details related to components associated with (e.g., included in) flexible assemblies are described below.

Although not shown, in some embodiments, the flexible assembly 120 can be configured to change between more than two configurations. For example, the flexible assembly 120 can be configured to move between a stowed configuration and a first deployed configuration, and between the first deployed configuration and a second deployed configuration. In some embodiments, the flexible assembly 120 can be configured to move between the stowed configuration and the second deployed configuration. Although not shown, in some embodiments, the flexible assembly 120 can be a steerable flexible assembly. In some embodiments, the flexible assembly 120 can be configured so that the flexible assembly 120 is steerable only when in a specified configuration (e.g., only steerable when in the deployed configuration). More details related to a steerable mechanism that can be used with a flexible assembly are described in co-pending U.S. patent application Ser. No. 12/121,345, filed May 15, 2008, entitled, "Articulating Torqueable Hollow Device," which has been incorporated herein by reference in its entirety.

FIG. 2A is a schematic diagram that illustrates an endoscopic assembly 200 that has two flexible assemblies 225 in a stowed configuration, according to an embodiment. Specifically, the flexible assemblies 225 are flexible assembly 220 and flexible assembly 222. As shown in FIG. 2A, the flexible assembly 220 has a component 230 and the flexible assembly 222 has a component 232. The component 230 and/or the component 232 can be, for example, a mechanical tool, an electromagnetic radiation source, and/or an electromagnetic radiation sensor.

As shown in FIG. 2A, the flexible assemblies 225 are disposed distal to and in front of an opening 212 of an endoscopic housing 210 (also can be referred to as an endoscopic tubular member) when in the stowed configuration. In some embodiments, each of the flexible assemblies 225 can be referred to individually as being in a stowed configuration (rather than being collectively referred to as being in a stowed configuration). In the embodiment shown in FIG. 2A, the flexible assembly 220 and the flexible assembly 222 are substantially parallel to one another when in the stowed configuration. In addition, the flexible assembly 220 is in contact with the flexible assembly 222 when in the stowed configuration. Although not shown, in some embodiments, each of the flexible assemblies 225 can be non-parallel to one another when in a stowed configuration and/or separated from one another when in a stowed configuration.

Figure 2B:
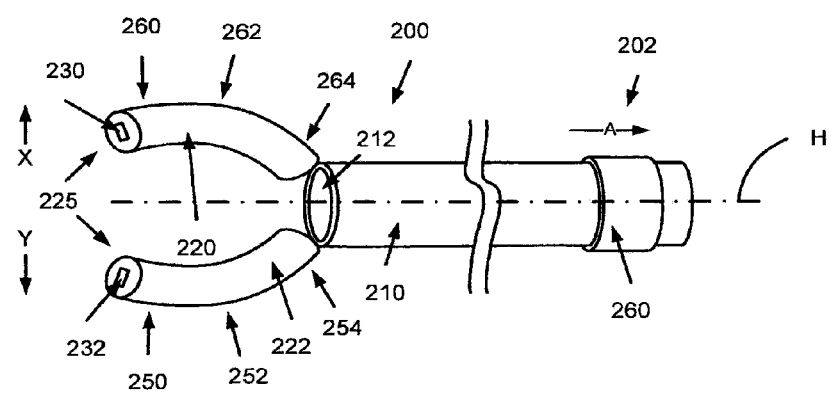
FIG. 2B is a schematic diagram that illustrates the flexible assemblies shown in FIG. 2A in a deployed configuration, according to an embodiment.

FIG. 2B is a schematic diagram that illustrates the flexible assemblies 225 shown in FIG. 2A in a deployed configuration, according to an embodiment. In some embodiments, each of the flexible assemblies 225 can be referred to individually as being in a deployed configuration (rather than being collectively referred to as being in a deployed configuration). Each of the flexible assemblies 225 are moved apart from one another when being moved from the stowed configuration to the deployed configuration. As shown in FIG. 2B, the flexible assembly 220 is moved away from a longitudinal axis H (or can also be a centerline) of the endoscopic housing 210 in a (e.g., along a) first direction that has a directional component X, and a distal portion 250 of the flexible assembly 230 is moved away from the longitudinal axis H of the endoscopic housing 210 in a second direction that has a directional component Y opposite the first direction. As shown in FIG. 2B, a shape defined by flexible assembly 220 is a mirror image of a shape defined by flexible assembly 222 (and vice versa) across the longitudinal axis H when in the stowed configuration and when in the deployed configuration.

Specifically, a distal portion 260 of the flexible assembly 220 is translated away from the longitudinal axis H in the first direction and rotated (with respect to the endoscopic housing 210 and the longitudinal axis H) in counter-clockwise fashion when moving from the stowed configured to the deployed configuration. A distal portion 250 of the flexible assembly 222 is translated away from the longitudinal axis H in the second direction and rotated in clockwise fashion when moving from the stowed configured to the deployed configuration. A medial portion 262 of the flexible assembly 220 is translated away from the longitudinal axis H in the first direction without rotating (with respect to the endoscopic housing 210 and the longitudinal axis H), and a medial portion 252 of the flexible assembly 222 is translated away from the longitudinal axis H in the second direction without rotating (with respect to the endoscopic housing 210 and the longitudinal axis H). A proximal portion 264 of the flexible assembly 220 is rotated in a clockwise direction away from the longitudinal axis H about an axis normal (or substantially normal) to the longitudinal axis H, and a proximal portion 255 of the flexible assembly 222 is rotated in a counter-clockwise direction away from the longitudinal axis H about an axis normal (or substantially normal) to the longitudinal axis H.

The flexible assemblies 225 are moved from the stowed configuration (shown in FIG. 2A) to the deployed configuration (shown in FIG. 2B) when an actuator 260 at a proximal end 202 of the endoscopic assembly 200 is moved in (e.g., moved along) a proximal direction (shown as direction A) from a first position (shown in FIG. 2A) to a second position (shown in FIG. 2B). The actuator 260 can be coupled to an actuator mechanism (not shown) such as one or more pull-wires) configured to cause the flexible assemblies 225 to move from the stowed configured to the deployed configuration. In some embodiments, the flexible assemblies 225, the actuator 260, and the actuator mechanism can be configured so that flexible assemblies 225 can be moved between the stowed configuration to the deployed configuration by moving the actuator 260 between the first position and the second position.

Although not shown, in some embodiments, the flexible assemblies 225 can be configured to move from the stowed configuration (shown in FIG. 2A) to the deployed configuration (shown in FIG. 2B) when the actuator 260 is moved in a direction different than direction A (e.g., moved in a proximal direction, rotated about longitudinal axis H). In some embodiments, an actuator used to cause movement of the flexible assemblies 225 can be any type of actuator and/or actuator mechanism such as, for example, a lever, a switch coupled to a motor, and/or so forth.

In some embodiments, the endoscopic assembly 200 can be configured so that the actuator 260 can only be used to move the flexible assemblies 225 from the stowed configuration to the deployed configuration (or vice versa), but not from the deployed configured to the stowed configuration (or vice versa). In such instances, the flexible assemblies 225 can be moved from the deployed configuration to the stowed configuration, for example, in response to an external applied force. For example, a user (e.g., an operator) of the endoscopic assembly 200 can insert the flexible assemblies 225, while in a stowed configuration, into a body of a patient through a working channel defined by a tube. After the flexible assemblies 225 are disposed within the body of the patient, the actuator 260 can be moved from the first position to the second position (and locked in the second position in some embodiments) by the user so that the flexible assemblies 225 of the endoscopic assembly 200 are moved from the stowed configuration to the deployed configuration (via pull-wires coupled to the actuator 260 and the flexible assemblies 225). The user of the endoscopic assembly 200 can release actuator 260 (so that tension on the actuator 260 will not keep the flexible assemblies 225 in the deployed configuration) and the flexible assemblies 225 can be configured (e.g., biased) so that the flexible assemblies 225 are collapsed from the deployed configured to the stowed configuration when the articulating members 225 come in contact with a side wall of the tube as the flexible assemblies 225 are being removed from the body of the patient.

In some embodiments, the endoscopic assembly 200 can be configured so that the actuator 260 can be used to move the flexible assemblies 225 from the stowed configuration to the deployed configuration (or vice versa), and one or more spring mechanisms (or bias mechanisms) coupled to (and/or disposed within) one or more of the flexible assemblies 225 can be configured to move the one or more flexible assemblies 225 from the deployed configuration to the stowed configuration (or vice versa) when the actuator 260 is released. In such instances, a force applied to the actuator 260 can be used to overcome a force exerted by the spring mechanism(s) so that the one or more flexible assemblies 225 can be moved from the stowed configuration to the deployed configuration. When the force applied to the actuator is released 260, the spring mechanism(s) can cause the one or more flexible assemblies 225 to move from the deployed configured to the stowed configuration. In some embodiments, the actuator 260 can be locked using one or more lock mechanisms (e.g., detent and groove, retractable pin, etc.) so that the one or more flexible assemblies 225 can remain in the deployed configuration and/or the stowed configuration until the lock mechanism(s) is/are released. More details related to pull-wires coupled to flexible assemblies are described below in connection with, for example, FIG. 6A through FIG. 7.

In some embodiments, one or more the flexible assemblies 225 can be moved from the deployed configuration to the stowed configuration using a tool. For example, a tool can be moved from within the endoscopic housing 210 and used to pull against at least a portion of the flexible assembly 220 to cause the flexible assembly 220 to move from the deployed configuration to the stowed configuration.

In some embodiments, the endoscopic assembly 200 can be configured so that one or more of the flexible assemblies 225 can be moved from the stowed configuration to the deployed configuration using a tool. For example, a tool can be moved from within the endoscopic housing 210 and pushed against the proximal portion 264 of flexible assembly 220 to cause the flexible assembly 220 to move from the stowed configuration to the deployed configuration. After the tool has been retracted into the endoscopic housing 210, the flexible assembly can be moved from the deployed configuration to the stowed configuration using, for example, the tool (and/or a different tool), a spring mechanism and/or an actuator (such as actuator 260).

The actuator 260 is configured to move the flexible assembly 220 and the flexible assembly 222 from the stowed configuration (shown in FIG. 2A) to the deployed configuration (shown in FIG. 2B) during overlapping time periods (e.g., during substantially the same time period (synchronously)). Although not shown, in some embodiments, the endoscopic assembly 200 can be configured so that the flexible assembly 220 and the flexible assembly 222 can be moved independently. For example, the flexible assembly 220 can be configured to move from a stowed configuration to a deployed configuration in response to actuation of a first actuator, and the flexible assembly 222 can be configured to move from a stowed configuration to a deployed configuration in response to actuation of a second actuator. In some embodiments the first actuator and the second actuator can be configured to that they can be coupled together and moved during overlapping time periods (e.g., during substantially the same time period).

Although not shown, in some embodiments, the flexible assemblies 225 can be configured so that more than one working channel defined by the endoscopic housing 210 can be exposed (when viewed from a distal end of the endoscopic assembly 200) when one or more of the flexible assemblies 225 are moved from the stowed configuration to the deployed configuration. In some embodiments, for example, a first working channel can be exposed when the flexible assembly 220 is moved from the stowed configuration to the deployed configuration, and a second working channel can be exposed when the flexible assembly 222 is moved from the stowed configuration to the deployed configuration. In some embodiments, the first working channel and the second working channel can be exposed (or uncovered) during mutually exclusive time periods or during overlapping time periods (e.g., during substantially the same time period) within a medical procedure.

Figure 3A:
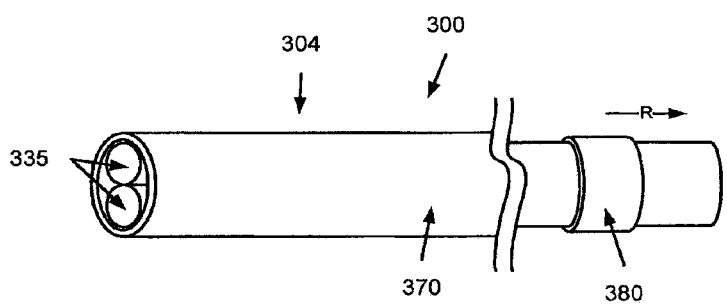
FIG. 3A is a schematic diagram that illustrates an endoscopic assembly that has a cover in a closed configuration and disposed around flexible assemblies, according to an embodiment.
Figure 3B:
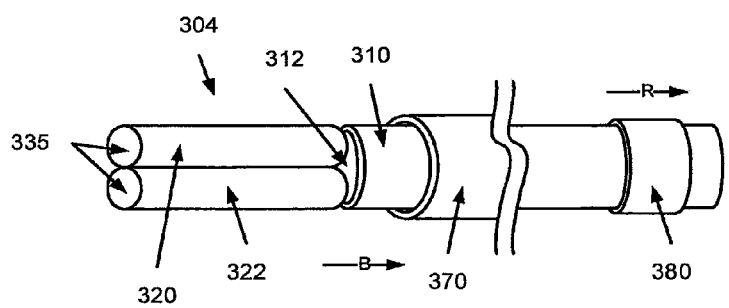
FIG. 3B is a schematic diagram that illustrates the cover shown in FIG. 3A in an open configuration, according to an embodiment.

FIG. 3A is a schematic diagram that illustrates an endoscopic assembly 300 that has a cover 370 in a closed configuration and disposed around flexible assemblies 335, according to an embodiment. FIG. 3B is a schematic diagram that illustrates the cover 370 shown in FIG. 3A in an open configuration, according to an embodiment.

As shown in FIG. 3A, the cover 370 can be configured so that the cover 370 can be disposed around the flexible assemblies 335 when the flexible assemblies 335 are in a stowed configuration. In some embodiments, the cover 370 can be disposed around the flexible assemblies 335 in the closed configuration to protect at least a portion of the flexible assemblies 335 when a distal end 304 of the endoscopic assembly 300 is inserted into, for example, a body of a patient. In some embodiments, the cover 370 can be configured to prevent one or more of the flexible assemblies 335 from being moved from the stowed configuration to the deployed configuration. Accordingly, the cover 370 can keep the flexible assemblies 335 from being moved in an undesirable fashion or damaged when being inserted into a body of a patient. In some embodiments, for example, the flexible assemblies 335 can be biased towards a deployed configuration and the cover 370 can be configured to keep the flexible assemblies 335 in a stowed configuration until the cover 370 is removed. In response to the cover 370 being removed, the flexible assemblies 335 can move to the deployed configuration. The flexible assemblies 335 can be moved back to (e.g., pushed back to) the stowed configuration by slidably moving the cover 370 over the flexible assemblies 335.

As shown in FIG. 3B, after the cover 370 has been moved from the closed configuration to the open configuration, one or more of the flexible assemblies 335 can move from a stowed configuration to a deployed configuration (because the cover 370 is no longer disposed around the flexible assemblies 335). In some embodiments, the cover 370 can be moved in (e.g., slidably moved along) a proximal direction (shown as direction B) so that the cover 370 is no longer disposed around the flexible assemblies 335. In some embodiments, the cover 370 can be moved in a proximal direction (shown as direction B) so that the cover 370 is entirely or partially disposed around an endoscopic housing 310. In some embodiments, the cover 370 can be moved from the closed configuration to the open configuration after the distal end 304 of the endoscopic assembly 300 has be inserted into, for example, a body of a patient. After the cover 370 has been moved to the open configuration, one or more of the flexible assemblies 335 can be moved to the deployed configuration within the body of the patient.

In some embodiments, the cover 370 can be moved between the closed configuration and the open configuration in response to an actuator 380 being moved in a proximal direction (shown as direction R). The actuator 380 can be different from an actuator (not shown in FIG. 3A or FIG. 3B)

used to move one or more of the flexible assemblies 335 between a stowed configuration and a deployed configuration. In some embodiments, the actuator 380 can be locked in the closed configuration and/or the open configuration using a lock mechanism (e.g., a releasable lock mechanism).

In some embodiments, the actuator 380 can be coupled to or can function as an actuator (not shown) used to move one or more of the flexible assemblies 335 so that the cover 370 and the one or more flexible assemblies 335 can be moved during overlapping time periods (e.g., simultaneously). For example, although not shown, the cover 370 can be moved from the closed configuration to the open configuration (and/or vice versa) and one or more of the flexible assemblies 335 can be moved from the stowed configuration to the deployed configuration (and/or vice versa), in response to the actuator 380 being moved. In other words, the endoscopic assembly 300 can be configured so that the cover 370 and one or more of the flexible assemblies 335 can be moved using a single actuator.

Although not shown, in some embodiments, the cover 370 can be moved between the closed configuration and the open configuration in response to an actuator 380 being moved in a direction different than direction R (e.g., moved in a distal direction, rotated about a centerline of the endoscopic assembly 300). In some embodiments, an actuator configured to cause movement of the cover 370 can be any type of actuator associated with an actuator mechanism such as, for example, a lever, a switch coupled to a motor, and/or so forth. In other words, the cover 370 can be configured to change from the closed configuration to the open configuration, and vice versa, in response to being actuated via, for example, a pull-wire, a motor, a lever, and/or so forth.

Although the cover 370 shown in FIG. 3A and FIG. 3B is a tube-shaped cover, in some embodiments, the cover 370 can be a different shape. For example, in some embodiments, a side wall of a cover associated with an endoscopic assembly can define one or more corners. Although not shown, in some embodiments, each of the flexible assemblies 335 can have a different cover. In some embodiments, the cover 370 can have a cap (not shown) configured to cover a distal end of the of the flexible assemblies 335. The cap can be configured to retract when the cover 370 is moved from the closed configuration to the open configuration.

Figure 4:
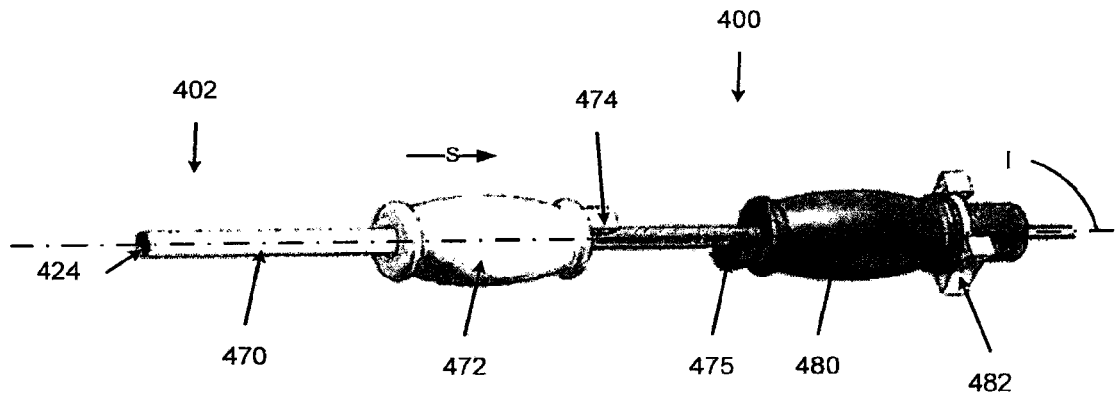
FIG. 4 is a schematic diagram that illustrates an endoscopic assembly, according to an embodiment.

FIG. 4 is a schematic diagram that illustrates an endoscopic assembly 400, according to an embodiment. As shown in FIG. 4, the endoscopic assembly 400 has a cover 470 disposed around one or more flexible assemblies 424, and the cover 470 is in a closed configuration. The cover 470 can be moved in a proximal direction (shown as direction S) from the closed configuration to an open configuration (not shown in FIG. 4) when a handle 472, which is coupled to the cover 470, is moved in the proximal direction from a first position (shown in FIG. 4) to a second position (not shown in FIG. 4). In some embodiments, the handle 472 can be referred to as an actuator.

When the handle 472 is in the second position, a notch component 474 of the handle 472 is configured to be coupled to a notch component 475 of handle 480 of the endoscopic assembly 400. In some embodiments, the handle 472 can be configured so that the handle 472 can be rotated about longitudinal axis I so that a portion of notch component 475 can be inserted into notch component 475. The notch component 474 can be coupled to notch component 475 so that handle 472 (and cover 470) cannot be readily moved in a distal direction (opposite direction S) away from handle 480. In some embodiments, the notch component 474 can be configured to be lockably coupled to notch component 475.

As shown in FIG. 4, an actuator 482 is in contact with the handle 480. The actuator 482 can be configured to cause one or more of the flexible assemblies 424 to move from a stowed configuration to a deployed configuration (not shown) when the actuator 482 is moved along direction S. In some embodiments, the actuator 482 can be configured to cause the flexible assemblies 424 to move from the deployed configuration to the stowed configuration when the actuator 482 is moved in a direction different from direction S. In some embodiments, the actuator 482 can be disposed around a proximal end portion of the handle 480.

Although not shown, in some embodiments, the actuator 482 can be coupled to the handle 472. In such instances, the actuator 482 (when coupled to handle 472) can be configured to cause (via an actuator mechanism that is not shown in FIG. 4) the flexible assemblies 424 to move from a stowed configured to a deployed configuration (not shown) when the handle 472 is moved along direction S. In some embodiments, the actuator 482 can be coupled to a different portion of the endoscopic assembly 400 other than the handle 472 or the handle 480. In some embodiments, the actuator 482 can be disposed between the handle 472 and the handle 480.

Although not shown, in some embodiments, the endoscopic assembly 400 can be configured so that handle 472, which is coupled to the cover 470, can be proximal to handle 480 (rather than distal to handle 480 as shown in FIG. 4). In such instances, the handle 472 can be coupled to the cover 470 via, for example, a pull-wire and/or a rod. The pull-wire and/or rod can be disposed outside of or within a lumen defined by the endoscopic assembly 400. In some embodiments, the endoscopic assembly 400 can be configured so that handle 472 can be proximal to actuator 482 (rather than distal to actuator 482 as shown in FIG. 4).

In some embodiments, the cover 470 can be moved from the closed configuration to the open configuration using the handle 472 after a distal end 402 of the endoscopic assembly 400 has been inserted into a body of a patient. Also, the notch component 474 can be coupled to the notch component 475 so that the handle 472 is coupled to the handle 480 after the distal end 402 of the endoscopic assembly 400 has been inserted into the body of the patient. In addition, the flexible assemblies 424 can be moved from a stowed configuration to a deployed configuration (not shown) when the actuator 482 is moved after the distal end 402 of the endoscopic assembly 400 has been inserted into the body of the patient.

Figure 5:
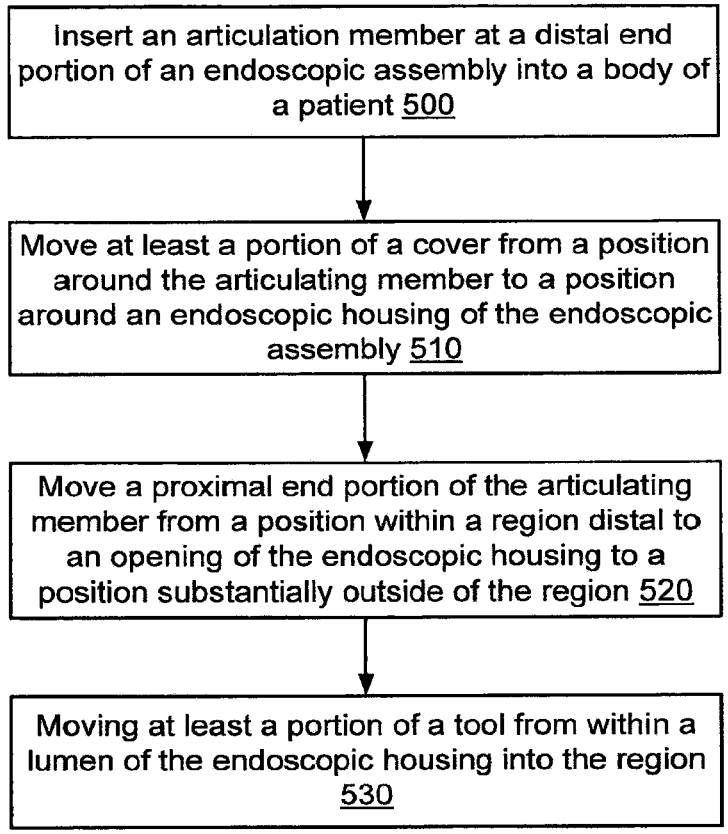
FIG. 5 is a flowchart that illustrates a method for using an endoscopic assembly, according to an embodiment.

FIG. 5 is a flowchart that illustrates a method for using an endoscopic assembly, according to an embodiment. As shown in FIG. 5, a flexible assembly at a distal end portion of an endoscopic assembly is inserted into a body of a patient, at 500. In some embodiments, the distal end portion of the endoscopic assembly can be inserted directly into the body of the patient via an incision or can be inserted into the body of the patient via a working channel defined by, for example, a tube disposed within an incision.

At least a portion of a cover is moved from a position around the flexible assembly to a position around an endoscopic housing of the endoscopic assembly, at 510. In some embodiments, the endoscopic housing can define a lumen (e.g., can be a tubular member that defines a lumen). In some embodiments, the cover can be in a closed configuration when the portion of the cover is in the position around the flexible assembly. In some embodiments, the cover can be in an open configuration when the portion of the cover is in the position around the endoscopic housing of the endoscopic assembly.

A proximal end portion of the flexible assembly is moved from a position within a region distal to an opening of the endoscopic housing to a position substantially outside of the region, at 520. In some embodiments, the region can be a volume distal to the opening of the endoscopic housing. In some embodiments, the region can be contiguous with at least a portion of a volume disposed within a lumen defined by the endoscopic housing. In some embodiments, the proximal end portion of the flexible assembly can be translated and/or rotatably moved from the position within the region to the position outside of the region. In some embodiments, a distal end portion and/or medial portion of the flexible assembly can be translated and/or rotatably moved from a position within the region to a position outside of the region. In some embodiments, the flexible assembly can be in a stowed configuration when the proximal end portion is within the region and can be in a deployed configuration when the proximal end portion is outside of the region.

At least a portion of a tool is moved from within a lumen of the endoscopic housing into the region, at 530. The portion of the tool can be moved from within the lumen and into the region during an endoscopic procedure. In some embodiments, the tool can be retracted into the endoscopic housing before the flexible assembly is changed from a deployed configuration to a stowed configuration and/or before the distal end portion of the endoscopic assembly is removed from the body of the patient.

Figure 6A:
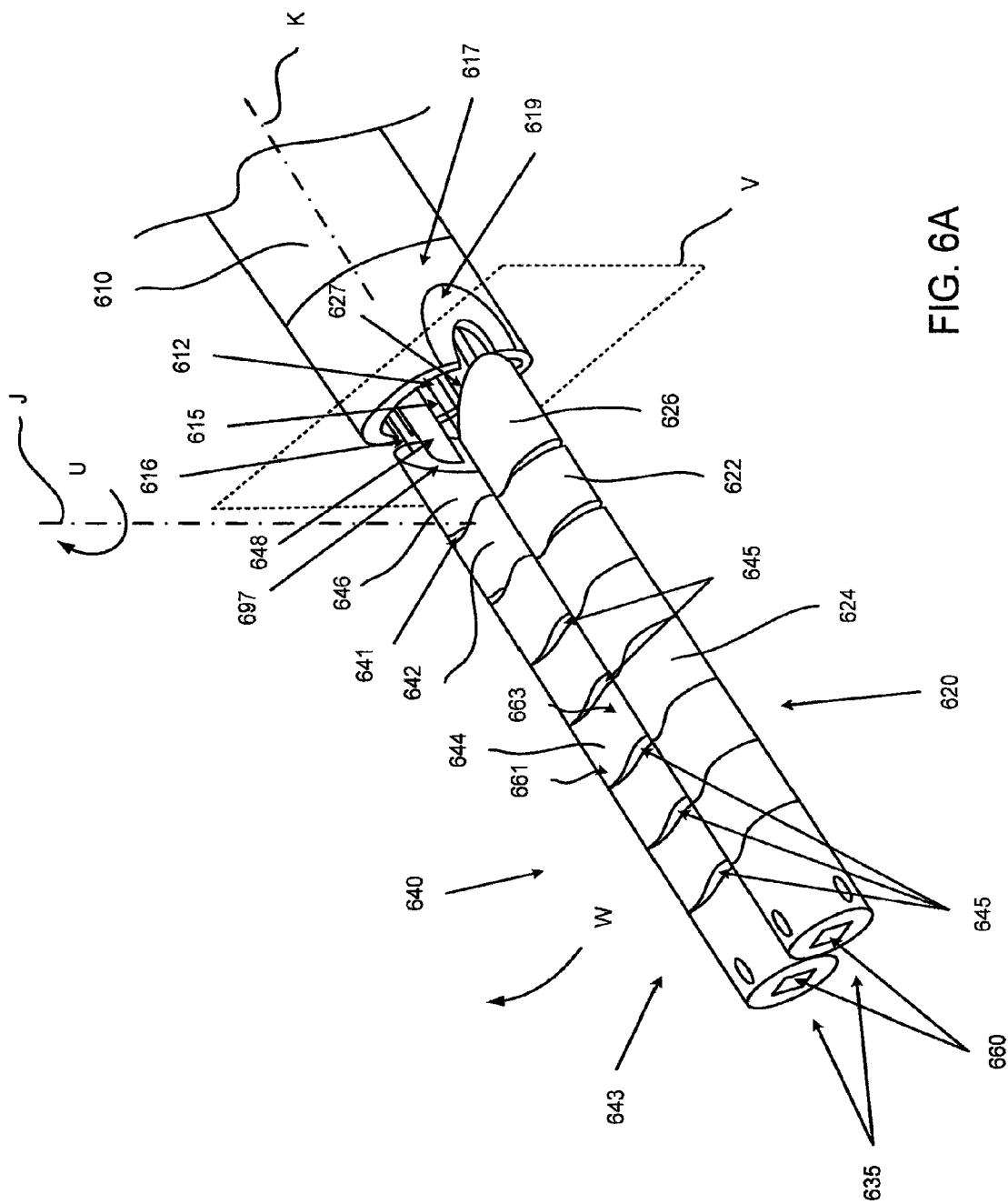
FIG. 6A is a schematic diagram that illustrates articulation assemblies that are each defined by a series of links and that are in a stowed configuration, according to an embodiment.
Figure 6B:
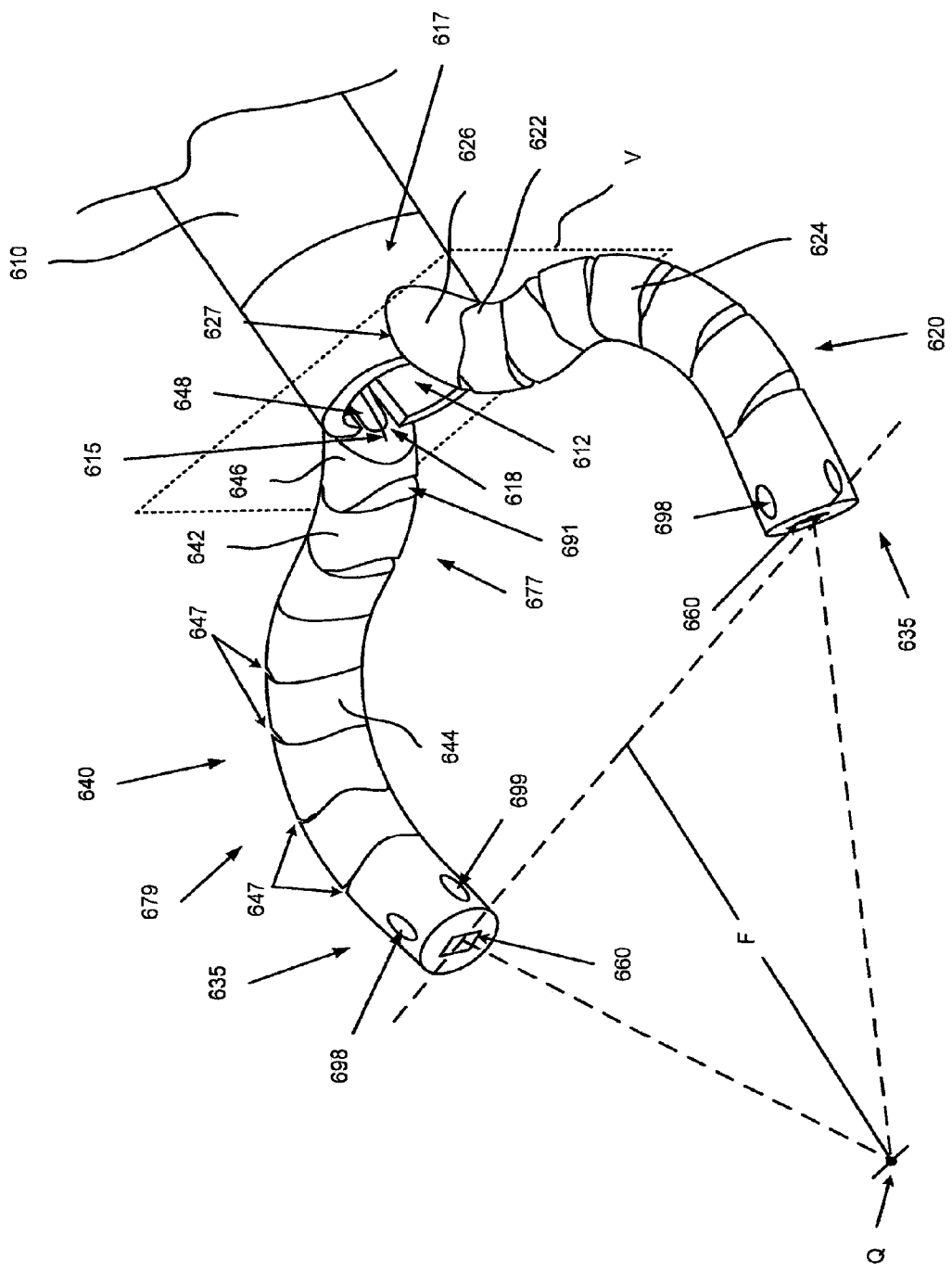
FIG. 6B is a schematic diagram that illustrates the articulation assemblies shown in FIG. 6A in a deployed configuration, according to an embodiment.

FIG. 6A is a schematic diagram that illustrates articulation assemblies 635 that are each defined by a series of links and that are in a stowed configuration, according to an embodiment. FIG. 6B is a schematic diagram that illustrates the articulation assemblies 635 shown in FIG. 6A in a deployed configuration, according to an embodiment. As shown in FIG. 6A and FIG. 6B, the articulation assemblies 635 include articulation assembly 640 and articulation assembly 620. Also, components 660 are coupled to the ends of the articulation assemblies 635.

As shown in FIG. 6A, the articulation assemblies 635 are disposed (or substantially disposed) distal to an opening 612 defined by an endoscopic housing 610. Specifically, proximal links (also can be referred to as proximal end links)—proximal link 646 and proximal link 626—of the articulation assemblies 635 are entirely disposed distal to the opening 612, which is aligned along plane V. Accordingly, the proximal links 646 and 626 are disposed distal to plane V. In some alternative embodiments, the endoscopic housing 610 can define an opening (such as opening 612) that is aligned along only a portion of and/or intersects a plane such as plane V. In some alternative embodiments, the respective proximal links (or other links distal to the proximal links) of the articulation assemblies 635 can be partially disposed distal to the opening 612 (and/or plane V) and partially disposed proximal to the opening 612 (and/or plane V). In some embodiments, one or more of the articulation assemblies 635 can be configured so that they are partially or entirely (e.g., substantially entirely) disposed within a volume that has a diameter equal to or less than an outside diameter of a wall 617 of the endoscopic housing 610 when the one or more of articulation assemblies 635 are in the stowed configuration.

As shown in FIG. 6B, at least a portion of the respective proximal links are disposed proximal to plane V when the articulation assemblies 635 are in the deployed configuration. For example, as shown in FIG. 6B, at least a portion of proximal link 626 is disposed proximal to the plane V when the articulation assembly 620 is in the deployed configuration. In some embodiments, one or more of the proximal links can be entirely (or substantially) disposed proximal to the plane V when one or more of the articulation assemblies 635 are in the deployed configuration. In some embodiments, one or more of the articulation assemblies 635 can have at least some links (e.g., links distal to the proximal links) with at least some portions disposed proximal to the plane V and other links with at least some portions disposed distal to the plane V when the one or more articulation assemblies 635 are in the deployed configuration.

As shown in FIG. 6B, all of the links defining the articulation assemblies 635, when in the deployed configuration, are entirely disposed outside of a volume distal to the endoscopic housing 610 and having an outer diameter equal to an inner diameter of the wall 617 of the endoscopic housing 610. In some embodiments, only a portion of one or more of the proximal links (and/or at least a portion of other links (e.g., links distal to the proximal links) included in the articulation assemblies 635) can be disposed outside of the volume when the articulation assemblies 635 are in the deployed configuration. As shown in FIG. 6A and FIG. 6B, the proximal link 626 has a flat side 627 configured to move around the wall 617 of the endoscopic housing 610 and against a flat portion 619 of the endoscopic housing 610 (shown in FIG. 6A and covered by the flat portion 627 in FIG. 6B) when the articulation assemblies 635 are moved from the stowed configuration to the deployed configuration.

As shown in FIG. 6A, the articulation assembly 640 is coupled to an outer pull-wire 616 and an inner pull-wire 615. The outer pull-wire 616 and the inner pull-wire 615 can collectively be used to move the articulation assembly 640 from the stowed configured to the deployed configuration (shown in FIG. 6B). Specifically, when the outer pull-wire 616 is pulled in a proximal direction during a first time period, gap 641 (on a proximal end of link 642), for example, can close and can cause a distal end 643 of the articulation assembly 640 to move along direction W. Pulling the outer pull-wire 616 can also cause link 642 to pivot about axis J along direction U (which is substantially orthogonal to a longitudinal axis K of the endoscopic housing 610) until gap 641 is closed. Accordingly, link 642 (and/or any of the other links) can be referred to as a rotatable member. Gap 691 (shown in FIG. 6B), which is on an opposite side of the articulation assembly 640 from gap 641, is opened during a time period overlapping with (e.g., substantially the same as) a time period during which gap 641 is closed. In addition, when the outer pull-wire 616 is pulled in the proximal direction, the proximal link 646 (e.g., a flat portion 697 of the proximal link 646) can be configured to move around the outside of the wall 617 of the endoscopic housing 610.

The inner pull-wire 615, when pulled in the proximal direction during a second time period after the first time period, can cause, for example, gaps 645 to close and can cause the distal end 643 of the articulation assembly 640 to move toward articulation assembly 620. The articulation assembly 640 can be moved to its final deployed configuration when the gaps 645 are closed. Gaps 647 (shown in FIG. 6B), which are on an opposite side of the articulation assembly 640 from gaps 645, can be opened during a time period overlapping with (e.g., substantially the same as) a time period during which gaps 645 are closed.

As shown in FIG. 6B, the outer pull-wire 615 has a distal end portion coupled to the articulation assembly 640 using a retention member 699. Although not shown, in some embodiments, any of the pull-wires (such as outer pull-wire 615) can be respectively coupled to the articulation assemblies 635 using, for example, an adhesive. Retention members 698 can be used to couple link wires (not shown) to the articulation assembly 640. As shown in FIG. 6A, the articulation assembly 640 is also coupled to a support member 648 which is disposed between the inner pull-wire 616 and the outer pull-wire 615. In some embodiments, the support member 648 may not be disposed between the inner pull-wire 616 and the outer pull-wire 615. For example, the support member 648 can be disposed above the inner pull-wire 616 and/or the outer pull-wire 615. In some embodiments, the inner pull-wire 616 can be disposed between the outer pull-wire 615 and the support member 648, or the outer pull-wire 615 can be disposed between the inner pull-wire 616 and the support member 648. More details related to link wires are described below in connection with FIG. 8.

In some embodiments, the endoscopic assembly can be configured so that the outer pull-wire 616 and the inner pull-wire 615 can be pulled during overlapping time periods to cause the articulation assembly 640 to move from a stowed configuration to a deployed configuration. In some embodiments, the outer pull-wire 616 and the inner pull-wire 615 can be pulled using the same actuator (and/or actuator mechanism) or using different actuators (and/or actuator mechanisms). More details related to pull-wires are described below in connection with FIG. 7 and FIG. 8.

As shown in FIG. 6A and FIG. 6B, one or more of the links that define the articulation assemblies 635 can be asymmetric. For example, an inner side 663 of link 644 can have a different shape than an outer side 661 of the link 644. Accordingly, when in the stowed configuration, gaps 645 are on the same side as one side of the link 644 of articulation assembly 640 and not on the same side as the other side of the link 644 of articulation assembly 640. Also, as shown in at least FIG. 6A, link 644 (and the adjacent links) can have an asymmetrical shape that is a different shape than, for example, the shape of link 642. More details related to links included in an articulation assembly are described in co-pending U.S. patent application Ser. No. 12/121,345, filed May 15, 2008, entitled, "Articulating Torqueable Hollow Device," which is incorporated herein by reference in its entirety.

As shown in FIG. 6A, the articulation assembly 640 is coupled to a support member 648. The support member 648 can be coupled to, for example, an inner portion of the wall 617 of the endoscopic assembly 610 (coupling not shown) and sufficiently stiff to keep the articulation assembly 640 distal to the plane V when the articulation assembly 640 is in a stowed configuration. Accordingly, the articulation assembly 640 (e.g., the proximal end proximal link 646) is not directly coupled to the endoscopic housing 610 at, for example, a pivot point. In some embodiments, the articulation assembly 640 can be coupled to the endoscopic housing 610 at a pivot point using, for example, a pin, a rivet and/or so forth. The support member 648 can be sufficiently flexible to bend when the articulation assembly 640 is moved from the stowed configuration to the deployed configuration.

In some embodiments, the support member 648 can be disposed within several links of the articulation assembly 640 or coupled only to the proximal link 646 without being coupled to other links that define the articulation assembly 640. In some embodiments, the support member 648 can define a lumen through which, for example, one or more wires coupled to one or more of the components 660 can be disposed. Control signals, data signals, and/or power can be transmitted and/or received using the wire(s).

As shown in FIG. 6B, the support member 648 can be configured to move into a notch 618 when the articulation assembly 640 is moved from the stowed configured to the deployed configuration. Similarly, the outer pull-wire 616 (not shown in FIG. 6B) and the inner pull-wire 615 can be moved into the notch 618 when the articulation assembly 640 is moved from the stowed configured to the deployed configuration. Although not specifically labeled and/or shown in FIG. 6A and/or FIG. 6B, the articulation assembly 620 can be similarly coupled to pull-wires and/or a support member(s).

As shown in FIG. 6B, one or more of the articulation assemblies 635 can be configured so that one or more of the components 660 are aimed in a specified direction when the one or more articulation assemblies 635 are in a deployed configuration. For example, if the components 660 are LEDs, the articulation assemblies 635 can be configured so that the component(s) 660 is aimed towards a target point Q (or a region (not shown)) that is a distance F distal to the components 660. If the components 660 are image sensors, the articulation assemblies 635 can be configured so that the field of view of the component(s) 660 is aimed towards the target point Q (or a region (not shown)) that is the distance F distal to the components 660. In some embodiments, the multiple image sensors can be used to define a stereoscopic image. In some embodiments, each of the articulation assemblies 635 can be configured so that each of the components 660 is aimed towards different target points (or regions) when the articulation assemblies 635 are in the deployed configuration.

Although not shown, multiple components (also can be referred to as a set of components) can be coupled to each of the articulation assemblies 635. For example, component 660 coupled to articulation assembly 620 can be, for example, an image sensor, and articulation assembly 620 can also have one or more light sources (not shown) coupled to a distal end of the articulation assembly 620. In some embodiments, the light source(s) can be, for example, an LED, a laser, a light bulb, and/or a fiber optic light source (e.g., a fiber optic configured to guide light emitted from an LED, a laser, a light bulb, and/or so forth). In some embodiments, the light source(s) (e.g., an LED, a distal end of a fiber optic) can be substantially aligned along or not aligned along a plane with the component 660 of the articulation assembly 620. In some embodiments, the light source(s) can be aimed towards a target point that is different than or the same as (e.g., substantially the same as) a target point of the image sensor. In some embodiments, any portion of a fiber optic light source can be disposed within and/or outside of, for example, the articulation assembly 620 and/or the endoscopic housing 610. For example, at least a portion of a fiber optic can be coupled to an outside portion of the articulation assembly 620 and at least a portion of a light source (e.g., an LED) associated with the fiber optic can be coupled to an inside portion of the endoscopic housing 610.

In some embodiments, a component (or set of components) coupled to each of the articulation assemblies 635 can be different. For example, the component 660 coupled to articulation assembly 620 can be a light source (e.g., a fiber optic light source), and the component 660 coupled to articulation assembly 640 can be an image sensor.

As shown in FIG. 6B, the articulation assemblies 635, when in the deployed configuration, have multiple inflection points. For example, the articulation assembly 640 has an inflection point 677 and an inflection point 679. Although not shown in FIG. 6B, in some embodiments, an articulation assembly can have more than two inflection points or less than two inflection points when in a deployed configuration and/or when in a stowed configuration.

Figure 7:
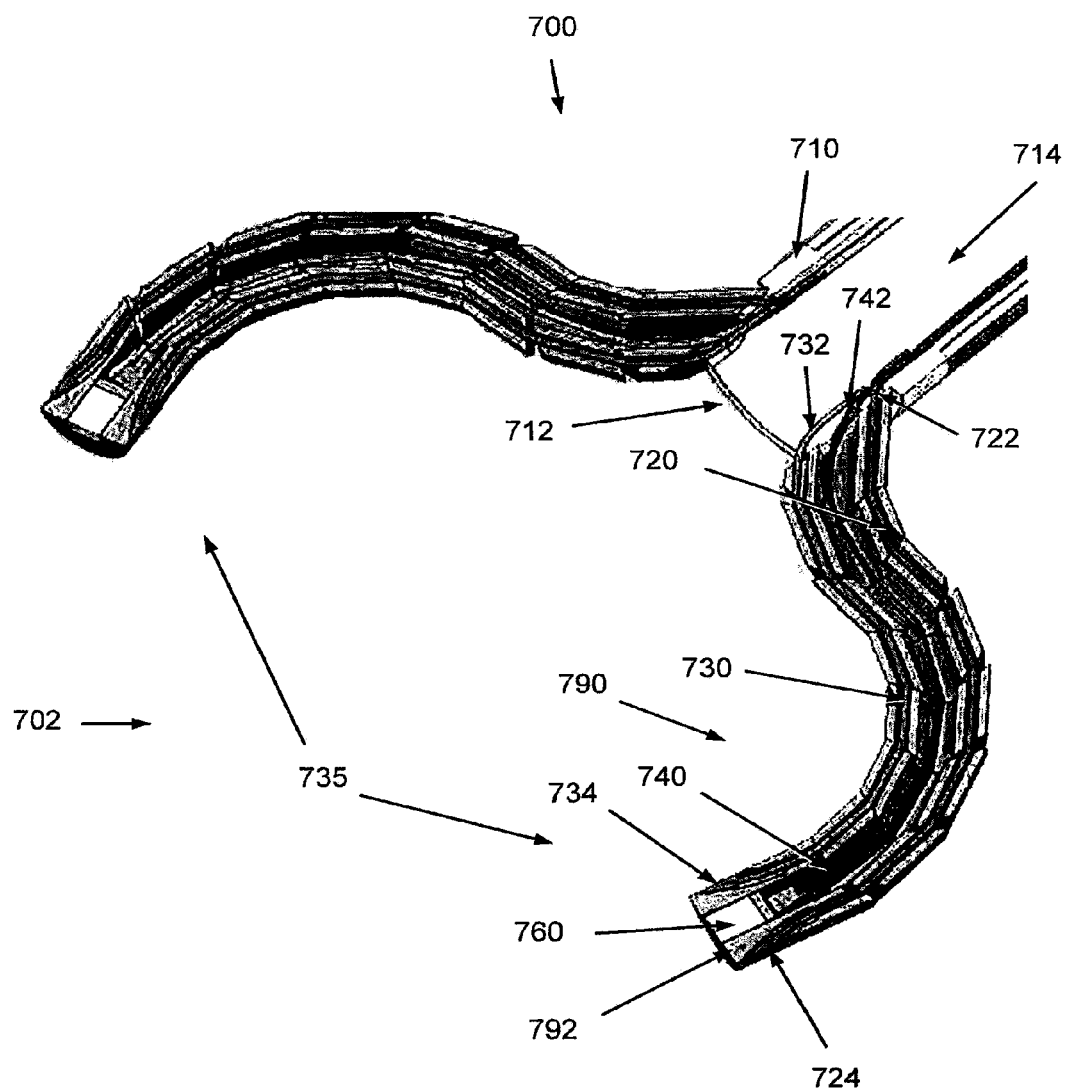
FIG. 7 is a schematic diagram that illustrates a cross-sectional view of articulation assemblies of an endoscopic assembly, according to an embodiment.

FIG. 7 is a schematic diagram that illustrates a cross-sectional view of articulation assemblies 735 of an endoscopic assembly 700, according to an embodiment. As shown in FIG. 7, the articulation assemblies 735 are in a deployed configuration. Articulation assembly 790 (from the articulation assemblies 735) has a component 760 that can be, for example, an image sensor and/or an electromagnetic radiation emitter. As shown in FIG. 7, links of the articulation assembly 790 define a lumen 740 through which at least one wire 742 coupled to the component 760 can be disposed. The wire 742 can be used to transmit, for example, a control signal to the component 760.

As shown in FIG. 7, an opening 712 defined by an endoscopic housing 710 can be accessed from a distal end 702 of the endoscopic assembly 700 when one or more of the articulation assemblies 735 (such as articulation assembly 790) are in a deployed configuration. Accordingly, a working channel 714 can be accessed from the distal end 702 of the endoscopic assembly 700. For example, the working channel 714 can be accessed from the distal end 702 during maintenance of at least a portion of the endoscopic assembly 700 and/or during a medical procedure using a tool separate from the endoscopic assembly 700. In some embodiments, the working channel 714 and/or the opening 712 cannot be accessed in a desirable fashion from the distal end 702 of the endoscopic assembly 700 when one or more of the articulation assemblies 735 are in a stowed configuration because the one or more articulation assemblies 735 can be disposed distal to the opening 712 (and can block the opening 712).

As shown in FIG. 7, the links of the articulation assembly 790 also define an inner channel 720 and an outer channel 730. In the embodiment shown in FIG. 7, an outer pull-wire 722 that can be used to move at least a portion of the articulation assembly 790 from a stowed configuration to a deployed configuration has at least a portion that is disposed within the inner channel 720. Similarly, an inner pull-wire 732 that can be used to move at least a portion of the articulation assembly 790 from a stowed configuration to a deployed configuration has at least a portion that is disposed within the outer channel 730.

As shown in FIG. 7, the outer pull-wire 722 has a distal end portion coupled to the articulation assembly 790 using a retention member 724 (e.g., a clip, a head, a protrusion, a knob) at a distal link 792 of the articulation assembly 790, and the inner pull-wire 732 has a distal end portion coupled to the articulation assembly 790 using a retention member 734 at the distal link 792 of the articulation assembly 790. The retention member 724 and/or the retention member 734 can be configured to fit within a recess of the distal link 792. Although not shown, in some embodiments, the outer pull-wire 722 and/or the inner pull-wire 732 can be coupled to the articulation assembly 790 using, for example, an adhesive. In some embodiments, the outer pull-wire 722 and/or the inner pull-wire 732 can be coupled to a link proximal to the distal link 792 of the articulation assembly 790. In some embodiments, the outer pull-wire 722 and/or the inner pull-wire 732 can be coupled to different links. For example, outer pull-wire 722 can be coupled to the distal link 792 of the articulation assembly 790 and inner pull-wire 732 can be coupled to a link proximal to the distal link 792 of the articulation assembly 790.

Figure 8:
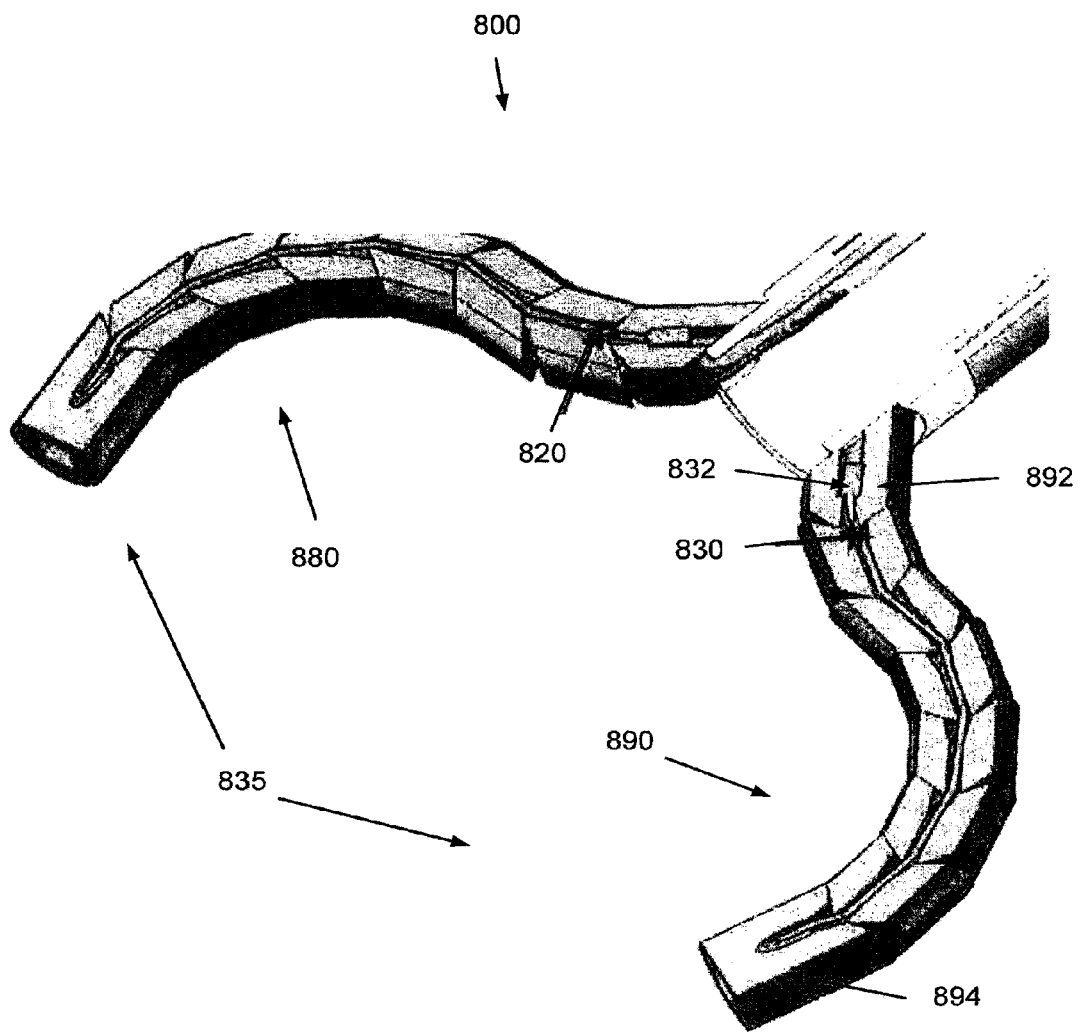
FIG. 8 is a schematic diagram that illustrates link wires within a cross-sectional view of articulation assemblies of an endoscopic assembly, according to an embodiment.

FIG. 8 is a schematic diagram that illustrates link wires within a cross-sectional view of articulation assemblies 835 of an endoscopic assembly 800, according to an embodiment. As shown in FIG. 8, the articulation assemblies 835, which include articulation assembly 880 and articulation assembly 890, are in a deployed configuration. A link wire 820 is disposed within a channel defined by links of the articulation assembly 880, and a link wire 830 is disposed within a channel defined by links of the articulation assembly 890. As shown in FIG. 8, the link wires are respectively disposed in an upper half of the articulation assemblies 835. Although not shown, in some embodiments, one or more links wires can also be included in a bottom half of one or more of the articulation assemblies.

The link wires are configured to respectively couple the links of the articulation assemblies 835 together. In other words, the link wires can each function as a tether configured to hold the links of their respective articulation assemblies 835 together. For example, the link wire 820 is configured to couple the links of the articulation assembly 880 so that they are not separated during operation (e.g., during movement from the deployed configuration to the stowed configuration).

As shown in FIG. 8, each of the link wires has a retention member. For example, link wire 830 has a retention member 832 included in a proximal link 892 of the articulation assembly 890. Although not shown in FIG. 8, the link wires are respectively coupled to the articulation assemblies 835 at a distal end of the articulation assemblies using a retention member. Although not shown, in some embodiments, each of the link wires can be adhesively coupled to one or more link within the articulation assemblies 835. In some embodiments, one or more of the link wires can be adhesively coupled to the articulation assemblies 835, respectively, in lieu of retention members. For example, link wire 830 can be adhesively coupled to multiple links of the articulation assembly 890.

Figure 9A:
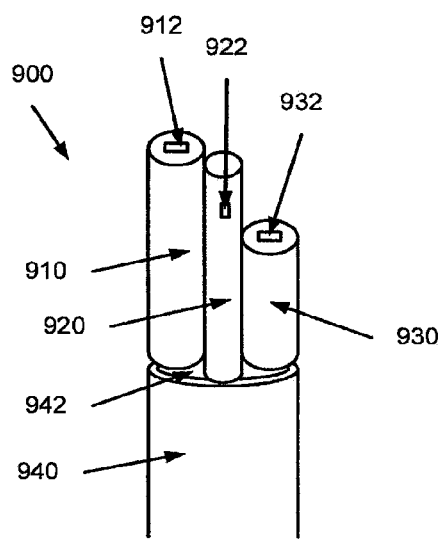
FIG. 9A is a schematic diagram that illustrates multiple articulation assemblies in a stowed configuration, according to an embodiment.

FIG. 9A is a schematic diagram that illustrates multiple articulation assemblies in a stowed configuration, according to an embodiment. The articulation assemblies, which include articulation assembly 910, articulation assembly 920, and articulation assembly 930, are disposed over an opening 942 defined by an endoscopic housing 940 of an endoscopic assembly 900. Articulation assembly 910 has a component 912, articulation assembly has a component 922, and articulation assembly 930 has a component 932. As shown in FIG. 9A, the articulation assemblies are different sizes. For example, articulation assembly 930 is shorter than articulation assembly 920, and articulation assembly 920 has an outer diameter smaller than an outer diameter of articulation assembly 910.

Figure 9B:
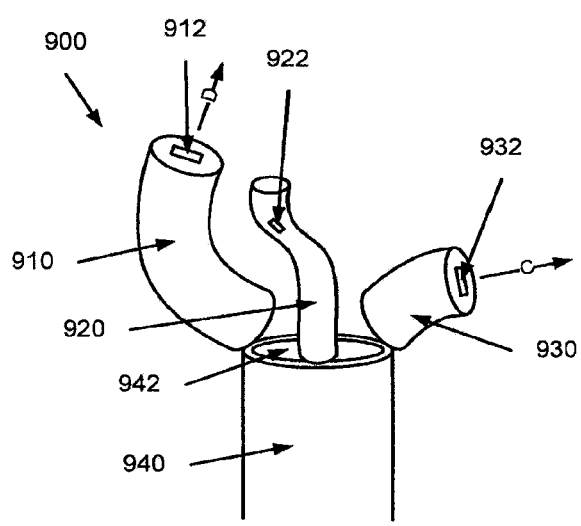
FIG. 9B is a schematic diagram that illustrates the articulation assemblies shown in FIG. 9A in a deployed configuration, according to an embodiment.

FIG. 9B is a schematic diagram that illustrates the articulation assemblies shown in FIG. 9A in a deployed configuration, according to an embodiment. More of the opening 942 is exposed (when viewed from a distal end of the endoscopic assembly 900) when the articulation assemblies are in the deployed configuration (shown in FIG. 9B) than is exposed when the articulation assemblies are in the stowed configuration (shown in FIG. 9A).

As shown in FIG. 9B, each of the articulation assemblies has a different deployed configuration than the other articulation assemblies. For example, the component 932 of the articulation assembly 930 has a distal surface that faces direction C (which is a substantially lateral direction (or in a direction that has a lateral component) from the endoscopic assembly 900) when the articulation assembly 930 is in a deployed configuration. In contrast, the component 912 of the articulation assembly 910 has a distal surface that faces direction D (which is a substantially distal direction from the endoscopic assembly 900) when the articulation assembly 910 is in a deployed configuration.

While various embodiments have been described above, it should be understood that they have been presented by way of example only, not limitation, and various changes in form and details may be made. Any portion of the apparatus and/or methods described herein may be combined in any combination. The embodiments described herein can include various combinations and/or sub-combinations of the functions, components and/or features of the different embodiments described. For example, a flexible assembly can be coupled to another flexible assembly of a medical device.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus, comprising:
an endoscopic housing having a distal end with a tip opening, the tip opening disposed along a plane substantially normal to a longitudinal axis of the endoscopic housing; and
a rotatable member coupled to the endoscopic housing and having a proximal portion configured to move from a stowed configuration to a deployed configuration when the proximal portion of the rotatable member is rotated about an axis substantially normal to the longitudinal axis of the endoscopic housing;
wherein the proximal portion of the rotatable member is disposed on a distal side of the plane when in the stowed configuration, and wherein the proximal portion of the rotatable member has a proximal surface configured to be in sliding contact with a flat, planar outer surface of a wall of the endoscopic housing when the rotatable member is moved to the deployed configuration.

2. The apparatus of claim 1, wherein the rotatable member is configured to move from the stowed configuration to the deployed configuration when the rotatable member is rotated in a first direction, and wherein the rotatable member is configured to move from the deployed configuration to the stowed configuration when the rotatable member is rotated in a second direction opposite the first direction.

3. The apparatus of claim 1, further comprising:
a pull wire coupled to the rotatable member and configured to move the rotatable member from the stowed configuration to the deployed configuration.

4. The apparatus of claim 1, further comprising:
an articulation assembly coupled to the endoscopic housing and defined by a plurality of links collectively coupled in series, wherein the rotatable member is a proximal end link of the plurality of links.

5. The apparatus of claim 1, wherein the rotatable member is included in an articulation assembly coupled to the endoscopic housing, the apparatus further comprising:
one of an electromagnetic radiation source and an electromagnetic radiation sensor coupled to a distal end portion of the articulation assembly.

6. The apparatus of claim 1, wherein the rotatable member is a first rotatable member, the first rotatable member being configured to rotate in a first direction about the longitudinal axis, the apparatus further comprising:
a second rotatable member having a proximal portion configured to move from the distal side of the plane to the proximal side of the plane when rotated in a second direction opposite the first direction.

7. The apparatus of claim 1, wherein the opening is in fluid communication with a working channel defined by the endoscopic housing.

8. The apparatus of claim 1, wherein the proximal portion of the rotatable member is disposed on a proximal side of the plane associated with the opening when in the deployed configuration.

9. The apparatus of claim 1, wherein the rotatable member is an articulation assembly including a plurality of links.

10. The apparatus of claim 1, wherein, when in the stowed configuration, a portion of the rotatable member is disposed within a space defined by the opening and distal to the opening of the endoscopic housing.

11. The apparatus of claim 10, wherein, when in the deployed configuration, the portion of the rotatable member is configured to be disposed outside of the space such that a portion of a tool moved from within a lumen of the endoscopic housing is disposed within the space.

12. The apparatus of claim 9, wherein the articulation assembly has two inflection points.

13. An apparatus, comprising:
an endoscopic housing having a distal end with a tip opening, the tip opening disposed along a plane substantially normal to a longitudinal axis of the endoscopic housing; and
a rotatable member coupled to the endoscopic housing and having a proximal portion configured to move from a stowed configuration to a deployed configuration when the proximal portion of the rotatable member is rotated about an axis substantially normal to the longitudinal axis of the endoscopic housing;
wherein the proximal portion of the rotatable member is disposed on a distal side of the plane when in the stowed configuration and disposed on a proximal side of the plane associated with the opening when in the deployed configuration, and
wherein the proximal portion of the rotatable member includes a substantially flat proximal surface that is non-parallel to the longitudinal axis of the endoscopic housing when the rotatable member is in the stowed configuration, and wherein the substantially flat proximal surface of the proximal portion of the rotatable member is substantially parallel to the longitudinal axis of the endoscopic housing when the rotatable member is in the deployed configuration.

* * * * *